United States Patent [19]

Yoshida et al.

[11] 4,233,401

[45] Nov. 11, 1980

[54] ANTIENZYME HOMOGENEOUS COMPETITIVE BINDING ASSAY

[75] Inventors: Robert A. Yoshida, Mountain View; Edward T. Maggio, Redwood City, both of Calif.

[73] Assignee: Syva Company, Palo Alto, Calif.

[21] Appl. No.: 815,487

[22] Filed: Jul. 14, 1977

[51] Int. Cl.$^2$ ...................... G01N 31/14; G01N 33/16
[52] U.S. Cl. ........................................ 435/7; 435/184; 435/810
[58] Field of Search .................. 195/103.5 A; 424/12

[56] References Cited

U.S. PATENT DOCUMENTS

| | | | |
|---|---|---|---|
| 3,817,837 | 6/1974 | Rubenstein et al. | 195/103.5 R |
| 3,935,074 | 1/1976 | Rubenstein et al. | 195/103.5 A |
| 3,998,943 | 12/1976 | Allman | 195/103.5 A |
| 4,020,151 | 4/1977 | Bolz et al. | 23/230 B |

OTHER PUBLICATIONS

Sternberger, Immunocyto Chemistry, 1974, pp. 129–135.
Dixon et al., Enzymes, 1964, pp. 316 and 317.
Cinader, "Antibodies to Enzymes —A Discussion of the Mechanisms of Inhibition and Activation", Antibodies to Biologically Active Molecules, Peyamon Press, (1967), p. 85.

Primary Examiner—Thomas G. Wiseman
Attorney, Agent, or Firm—Bertram I. Rowland

[57] ABSTRACT

Methods and reagent combinations are provided for competitive protein binding assays for determining a member of an immunological pair (ligand and receptor) whereby an enzyme-ligand conjugate is employed in combination with an enzyme inhibitor, conveniently an antibody to said enzyme. When ligand is the analyte, receptor for ligand is also included in the assay medium, while supplemental amounts of receptor need not be added when receptor is the analyte. The assay is carried out in an aqueous buffered medium, normally at constant temperature, by combining in the assay medium the unknown sample suspected of containing the analyte, enzyme-bound-ligand, ligand receptor (antiligand), enzyme inhibitor (antienzyme), and enzyme substrates, and the enzymatic activity in the assay medium determined. By comparing the observed enzymatic activity with an unknown to the enzymatic activity observed in an assay medium with a known amount of analyte, the amount of analyte can be quantitatively determined.

Kits are provided having matched amounts of enzyme-bound-ligand, antienzyme and, when appropriate, antiligand for use in the subject assay.

23 Claims, No Drawings

ANTIENZYME HOMOGENEOUS COMPETITIVE BINDING ASSAY

BACKGROUND OF THE INVENTION

1. Field of the Invention

There is a present increasing interest and need in being able to assay or monitor a wide variety of organic compounds. Included among compounds of interest are drugs which are employed in the treatment of diseases or aberrant conditions, drugs of abuse, naturally occurring compounds involved with bodily functions, pollutants, trace contaminants and the like. The concentrations of interest of most of these compounds are generally of the order of 1 $\mu$g/ml or less. In many instances, the environment in which these compounds are found include one or more compounds of similar structure, which must be distinguished from the compound of interest.

A body of techniques which have evolved are referred to as competitive protein binding assays. These assays rely on the ability of a receptor, usually an antibody, to recognize a specific spatial and charge conformation. The binding of the receptor to a ligand allows for a discrimination between bound and unbound ligand. By employing a labeled ligand and allowing for competition between labeled ligand and ligand in the unknown for the receptor, one obtains a distribution of the receptor between labeled and unlabeled ligand. By employing appropriate labels, one can distinguish between bound labeled ligand and unbound labeled ligand so as to relate this ratio to the amount of ligand in the unknown. When receptor is to be measured, substantially the same technique is employed, except that receptor is not added and one need not add unlabeled ligand.

In developing competitive protein binding assays a number of factors must be considered. Ease of preparation of the various reagents is an important consideration. The manipulative steps involved in the assay are also important, since it is desirable to minimize the opportunities for operator error. Stability of the reagents is also a significant consideration, as well as compatability of the system with presently available equipment. Of course, one is also interested in the accuracy and dependability with which the small concentrations of the materials are measured.

2. Description of the Prior Art

U.S. Pat. No. 3,817,837 teaches a homogeneous enzyme immunoassay. U.S. Pat. Nos. 3,654,090, 3,791,932, 3,850,752 and 3,839,153 teach heterogeneous enzyme immunoassays. In the agenda for the Ninth Annual Symposium on Advanced Analytical Concepts for the Clinical Laboratory, Mar. 17 and 18, 1977, Oakridge National Laboratory, a paper entitled "Phospholipase C-Labeled Antihuman IgG: inhibition of enzyme activity by human IgG," presented by R. Wei and S. Reib is reported. U.S. Pat. Nos. 3,935,074 and 3,998,943 disclose immunoassay techniques involving steric inhibition between two different receptors for different epitopic sites. Carrico et al, Anal. Biochem. 72, 271 (1976) and Schroder, et al, ibid 72, 283 (1976) teach competitive protein binding assays where a label is bonded to a hapten with the label being subject to enzymatic transformation to produce a signal. Antibody bound to the hapten inhibits the approach of enzyme to the label.

SUMMARY OF THE INVENTION

Competitive protein binding methods and composition combinations for use in the methods are provided for determining an analyte which is a member of an immunological pair (ligand and receptor). The methods depend on the use of an enzyme-bound-ligand and an enzyme inhibitor which is sterically prevented from inhibiting the enzyme when ligand receptor (antiligand) is bound to the ligand of the enzyme-bound-ligand. When ligand is the analyte, antiligand is included in the medium, while no antiligand need be added when antiligand is the analyte.

The assay is carried out in an aqueous buffered medium and various protocols may be employed where the antiligand and enzyme inhibitor are added concomitantly or successively. The enzymatic activity may be determined by adding enzyme substrates to the assay media. By comparing the enzymatic activity determined with a unknown with that determined with a known amount of analyte, the amount of analyte in the unknown can be semiquantitatively or quantitatively determined.

Reagent combinations are provided which are matched for the subject assay and include enzyme-bound-ligand and enzyme inhibitor, and when ligand is the analyte, antiligand. Other materials may also be included, such as stabilizers, preservatives, buffers, etc.

DESCRIPTION OF THE SPECIFIC EMBODIMENTS

Sensitive, accurate, competitive protein binding assays are provided employing an enzyme label, where the enzymatic activity in the assay medium is related to the amount of analyte present in the assay medium. The method employs a conjugate of an enzyme and ligand, where the enzyme-bound-ligand retains a substantial proportion of its enzymatic activity, up to 100% of the activity of the enzyme-bound-ligand, when receptor for the ligand is bound to the ligand conjugated to the enzyme. An enzyme inhibitor is employed, which substantially reduces the enzyme activity. In the subject method, the approach of the enzyme inhibitor to the enzyme is obstructed by the presence of ligand receptor bound to the ligand of the enzyme-bound-ligand. In ligand assays, the amount of antiligand which is bound to the enzyme-bound-ligand will be affected by the amount of ligand present in the assay medium, while in antiligand assays, the amount of antiligand in the assay medium will directly relate to its amount in the unknown sample. Conveniently, the enzyme inhibitor can be an antibody to the enzyme which is capable of inhibiting the enzyme activity when bound to the enzyme. The enzyme-bound-ligand will have a sufficient number of epitopic sites to obstruct the approach of the enzyme inhibitor when these sites are saturated with antiligand.

Definitions

Analyte-the compound or composition to be measured, which may be mono- or polyepitopic, antigenic or haptenic, a single or plurality of compounds which share at least one common epitopic site or a receptor.

Ligand-any organic compound for which a receptor naturally exists or can be prepared.

Ligand Analog-a modified ligand which can compete with the analogous ligand for receptor, the modification providing means to join the ligand analog to an enzyme or other molecule.

Receptor-any compound or composition capable of recognizing a particular spatial and polar organization of a molecule i.e. an epitopic site, and normally polyvalent i.e. having at least two binding sites. Illustrative receptors include naturally occurring receptors, antibodies, enzymes, lectins, Fab fragments, and the like. For any specific ligand, the receptor will be referred to as antiligand, for example, an antibody for an enzyme will be referred to as antienzyme. The receptor and its reciprocal ligand form an immunological pair.

Enzyme-bound-ligand-a conjugate having at least one enzyme molecule covalently bonded to at least one ligand analog, whereby the enzyme retains a substantial proportion of its enzymatic activity when antiligand saturates the available epitopic sites and the binding of antiligand to the ligand epitopic sites obstructs the binding of enzyme inhibitor.

Enzyme Inhibitor-a macromolecule capable of substantially inhibiting enzymatic activity when bound to an enzyme, its inhibition being either reversible or irreversible, and is impeded from inhibiting said enzyme when receptor is bound to enzyme-bound-ligand. Conveniently, the enzyme inhibitor may be an antibody which recognizes a specific enzyme and when bound to the enzyme substantially reduces the enzymatic activity of the enzyme or a substrate which binds to the enzyme and diminishes the measured enzymatic activity.

Assay

The subject assay is carried out in an aqueous zone at a moderate pH, generally close to the pH for optimizing the response to changes in analyte concentration. The assay zone for the determination of analyte is prepared by employing an appropriately buffered aqueous solution, the unknown sample, which may have been subject to prior treatment, enzyme-bound-ligand, enzyme inhibitor, antiligand for ligand assays, and enzyme substrates. The assay zone will normally be homogeneous.

The aqueous medium may include other polar solvents, usually oxygenated organic solvents of from 1 to 6, more usually of from 1 to 4 carbon atoms, including alcohols, ethers and the like. Usually these cosolvents will be present in less than about 20 weight percent, more usually in less than about 10 weight percent.

The pH for the medium will usually be in the range of from about 5 to 10, more usually in the range of from about 7 to 9 and preferably from about 7 to 8.5. Various buffers may be used to achieve the desired pH and maintain the pH during the determination. Illustrative buffers include borate, phosphate, carbonate, tris, barbital, and the like. The particular buffer employed is not critical to this invention, but in individual assays one buffer may be preferred over another.

Moderate temperatures are normally employed for carrying out the assay and usually constant temperatures during the period of the assay measurement will be employed. The temperatures will normally be in the range of from about 10° to 50° C., more usually from about 15° to 40° C.

The concentration of analyte which may be assayed will generally vary from about $10^{-4}$ to $10^{-15}$M, more usually from about $10^{-6}$ to $10^{-13}$M. Considerations such as whether the assay is qualitative, semiquantitative or quantitative, the particular enzyme and method of detection of enzymatic activity, and the concentration of the analyte of interest will normally determine the concentration of the other reagents. In a competitive mode where the enzyme inhibitor and antiligand are competing for sterically excluded sites, the relative concentrations of the two materials is quite important. Contrastingly, where the antiligand is added first, and allowed to approach equilibrium followed by addition of enzyme inhibitors, the relative concentration of the two materials is less significant.

The amount of antiligand employed is normally calculated based on receptor sites and will vary with the concentration of enzyme-bound-ligand, the ratio of ligand to enzyme in the enzyme-bound-ligand and the affinity of the receptor for the ligand. Usually, there will be at least one active receptor site per molecule of enzyme-bound-ligand and less than about 20 active sites per epitopic site of ligand as enzyme-bound-ligand, but receptor-ligand epitopic site ratios may be as high as a 100 to 1, depending on the type of assay and the affinity of the receptor. Preferably, the ratio of receptor binding sites to epitopic sites of ligand as enzyme-bound-ligand will be at least 1, usually at least 2, and not more than about 5 to 1.

The ratio of enzyme to ligand in the enzyme-bound-ligand will vary widely depending upon the enzyme, particularly the molecular weight of the enzyme and available binding sites, and the molecular weight of the ligand. For haptenic ligands, those under 2,000 usually under 1,200 molecular weight, there will be on the average at least one ligand per enzyme, usually not more than about one per 2,000 molecular weight of the enzyme and usually not more than one per 5,000 molecular weight of the enzyme, particularly for enzymes below 50,000 molecular weight. For antigenic ligands, usually having molecular weights in excess of 2,000, more usually in excess of 5,000, the possibility of having a plurality of enzymes to one ligand exists. The weight ratio of enzyme to ligand may vary from about $10^{-6}$–$10^2$:1, usually from about $10^{-2}$–$10^2$:1. Since a ligand may be a virus or a cell, the number of enzymes to such a large ligand could be large as to the mole ratio and very small as to weight ratio. With ligands having molecular weights in the range of 10,000 to 600,000, there will usually be on the average at least one enzyme per ligand, and not more than one enzyme per 5,000 molecular weight of ligand.

The concentrations of the enzyme-bound-ligand and the receptor (based on binding sites) may vary widely, generally being from about $10^{-4}$ to $10^{-14}$ M, more usually from $10^{-6}$ to $10^{-12}$ M. The molar ratio of enzyme-bound-ligand to the maximum concentration of interest for the ligand will generally be from about $10^{-4}$–10:1, more usually from about $10^{-3}$–1:1.

The equivalent ratio of enzyme inhibitor to enzyme based on active sites will usually be at least about 0.1, more usually at least 1, and may be in molar excesses of 100 or more.

In any particular assay, various proportions of the reagents will be tested so as to determine the ratios which provide the optimum sensitivity. The particular ratios will not only vary with the protocol for the assay, but with each ligand, each enzyme, the ratios of enzyme to ligand in the enzyme-bound-ligand, the concentration range of interest, and the like.

The protocols for the subject assay may vary widely depending on the nature of the materials, the desired sensitivity, and the nature of the involved equipment. Either a competitive or equilibrium mode may be employed. In the competitive mode, both the antiligand and the enzyme inhibitor compete for the enzyme-bound-ligand. In the equilibrium mode, the antiligand is allowed to interact with the enzyme-bound-ligand for a sufficient time to approach an equilibrium, after which time the enzyme inhibitor may be added. The enzyme inhibitor can then only react with enzyme from which it is not sterically inhibited from approaching by the presence of the antiligand.

In the competitive protocol for ligand, the antiligand and enzyme inhibitor may be added concomitantly to the ligand and enzyme-bound-ligand, conveniently as a single reagent, to the assay medium containing the enzyme substrates and the enzymatic activity determined at two different times measured from the time of addition of the reagents. The difference in these two values can be compared to values obtained with known amounts of the ligand. Alternatively, the substrates can be added after the addition of the reagents and the time calculated from the addition of the reagents. Various incubation times can be employed between the addition of the reagents and the measurement.

In the equilibrium mode for ligand, the antiligand will be added to the ligand concomitantly with the enzyme-bound-ligand or followed by the addition of the enzyme-bound-ligand. In a first mode, after addition of the antiligand and enzyme-bound-ligand, the assay medium may be incubated for a sufficient time to approach equilibrium, followed by addition of the enzyme inhibitor. The medium may then be incubated a second time followed by measurements for enzymatic activity. Alternatively, the antiligand may be added to the sample and incubated, followed by the addition of the enzyme-bound-ligand and a further incubation, followed by the addition of the enzyme inhibitor and optionally a third incubation. While one measurement may suffice, it is preferable to take two spaced apart measurements for each assay and report the results as the difference between the two values. In particular situations, protocols other than those described above may be employed.

The incubation times will vary widely, and may be less than about 0.5 minute and usually not exceeding 24 hours, more usually not exceeding 6 hours, and preferably not exceeding about 30 minutes. Since the ultimate result will be dependent upon the results obtained with standard(s) treated in substantially the same manner and when possible in the identical manner, the particular mode and periods of time are not critical, so long as significant reproducible differentiations are obtained with varying concentrations of analyte.

Depending upon the choice of assay protocol, equipment employed and the concentration of analyte involved, assay volumes may be as small as about 1 µl, more usually being at least 25 µl, and will usually not exceed 5 ml, more usually not exceeding about 2 ml.

In a particular variation, the enzyme inhibitor may be a Fab fragment of antienzyme. In this mode, it is feasible to combine the enzyme-bound-ligand and the Fab antienzyme fragment as a single reagent, so that the reagents may be prepared at a predetermined ratio. By combining these reagents in bulk, the opportunity for measuring errors is diminished.

In determining antiligand, the procedure is substantially the same as described above, except that enzyme-bound-ligand may be added first to the sample and incubated, followed by addition of enzyme inhibitor.

Materials

The primary components in the subject assay for analyte are: the analyte; enzyme-bound-ligand; enzyme inhibitor; and enzyme substrates.

Analyte

The ligand analytes of this invention are characterized by being monoepitopic or polyepitopic. The polyepitopic ligand analytes will normally be poly(amino acids) i.e. polypeptides and proteins, polysaccharides, nucleic acids and combination thereof. Such combinations or assemblages include bacteria, viruses, chromosomes, genes, mitochondria, nucleii, cell membranes and the like.

For the most part, the polyepitopic ligand analytes employed in the subject invention will have a molecular weight of at least about 5,000, more usually of at least about 10,000. In the poly(amino acid) category, the poly(amino acids) of interest will generally be of from about 5,000 to 5,000,000 molecular weight, usually from about 20,000 to 1,000,000 molecular weight; among proteins of interest are those of from about 5,000 to 600,000 molecular weight, which include albumins and globulins; among the hormones of interest, the molecular weights will generally range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:
protamines
histones
albumins
globulins
scleroproteins
phosphoproteins
mucoproteins
chromoproteins
lipoproteins
nucleoproteins
unclassified proteins, e.g. somatotropin, prolactin, insulin, pepsin A number of proteins found in the human plasma are important clinically and include:
Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
  $\alpha_1$-glycoprotein
$\alpha_1$X-Glycoprotein
Thyroxin-binding globulin
Inter-$\alpha$-trypsin-inhibitor
Gc-globulin
  (Gc 1-1)
  (Gc 2-1)
  (Gc 2-2)
Haptoglobin
  (Hp 1-1)
  (Hp 2-1)
  (Hp 2-2)
Ceruloplasmin
Cholinesterase
$\alpha_2$-Lipoprotein(s)
$\alpha_2$-Macroglobulin $\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G
    (IgG) or $\gamma$G-globulin
Mol. formula:
    $\gamma_2\kappa_2$ or $\gamma_2\lambda_2$
Immunoglobulin A (IgA)
    or $\gamma$A-globulin
Mol. formula:
    $(\alpha_2\kappa_2)^n$ or $(\alpha_2\lambda_2)^n$
Immunoglobulin M
    (IgM) or $\gamma$M-globulin
Mol. formula:
    $(\mu_2\kappa_2)^5$ or $(\mu_2\lambda_2)^5$
Immunoglobulin D(IgD) or $\gamma$D-Globulin ($\gamma$D)
Mol. formula: $(\delta_2\kappa_2)$ or $(\delta_2\lambda_2)$
Immunoglobulin E (IgE)
    or $\gamma$E-Globulin ($\gamma$E)
Mol. formula: $(\epsilon_2\kappa_2)$ or $(\epsilon_2\lambda_2)$
Free K and $\gamma$ light chains
Complement factors:
C'1
    C'1q
    C'1r
    C'1s
C'2
C'3
    $\beta_1$A
    $\alpha_2$D
C'4
C'5
C'6
C'7
C'8
C'9

Important blood clotting factors include:

TABLE VII

BLOOD CLOTTING FACTORS

| International designation | Name |
|---|---|
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:

Peptide and Protein Hormones

Parathyroid hormone
    (parathormone)
Thyrocalcitonin
Insulin
Glucagon
Relaxin
Erythropoietin
Melanotropin
    (melanocyte-stimulating
    hormone; intermedin)
Somatotropin
    (growth hormone)
Corticotropin
    (adrenocorticotropic hormone)
Thyrotropin
Follicle-stimulating hormone
Luteinizing hormone
    (interstitial cell-stimulating hormone)
Luteomammotropic hormone
    (luteotropin, prolactin)
Gonadotropin
    (chorionic gonadotropin)

Tissue Hormones

Secretin
Gastrin
Angiotensin I and II
Bradykinin
Human placental lactogen

Peptide Hormones from the Neurohypophysis

Oxytocin
Vasopressin
Releasing factors (RF)
    CRF, LRF, TRF, Somatotropin-RF,
    GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
|---|---|
| *Streptococcus pyogenes* | Polysaccharide |
| *Diplococcus pneumoniae* | Polysaccharide |
| *Neisseria meningitidis* | Polysaccharide |
| *Neisseria gonorrhoeae* | Polysaccharide |
| *Corynebacterium diphtheriae* | Polysaccharide |
| *Actinobacillus mallei;* | Crude extract |
| *Actinobacillus whitemori* | |
| *Francisella tularensis* | Lipopolysaccharide |
| | Polysaccharide |
| *Pasteurella pestis* | |
| *Pasteurella pestis* | Polysaccharide |
| *Pasteurella multocida* | Capsular antigen |
| *Brucella abortus* | Crude extract |
| *Haemophilus influenzae* | Polysaccharide |
| *Haemophilus pertussis* | Crude |
| *Treponema reiteri* | Polysaccharide |
| *Veillonella* | Lipopolysaccharide |
| *Erysipelothrix* | Polysaccharide |
| *Listeria monocytogenes* | Polysaccharide |
| *Chromobacterium* | Lipopolysaccharide |
| *Mycobacterium tuberculosis* | Saline extract of 90% phenol extracted mycobacteria and polysaccharide fraction of cells and tuberculin |
| *Klebsiella aerogenes* | Polysaccharide |
| *Klebsiella cloacae* | Polysaccharide |
| *Salmonella typhosa* | Lipopolysaccharide, Polysaccharide |
| *Salmonella typhi-murium;* | Polysaccharide |
| *Salmonella derby* | |
| *Salmonella pullorum* | |

-continued

| Species of Microorganisms | Hemosensitin Found in |
|---|---|
| *Shigella dysenteriae* | Polysaccharide |
| *Shigella flexneri* | |
| *Shigella sonnei* | Crude, polysaccharide |
| Rickettsiae | Crude extract |
| *Candida albicans* | Polysaccharide |
| *Entamoeba histolytica* | Crude extract |

The microorganisms which are assayed may be intact, lysed, ground or otherwise fragmented, and the resulting composition or portion, e.g. by extraction, assayed. Microorganisms of interest include:

Corynebacteria

*Corynebacterium diptheriae*

Pneumococci

*Diplococcus pneumoniae*

Streptococci

*Streptococcus pyogenes*
*Streptococcus salivarus*

Staphylococci

*Staphylococcus aureus*
*Staphylococcus albus*

Neisseriae

*Neisseria meningitidis*
*Neisseria gonorrheae*

| Enterobacteriaciae | |
|---|---|
| *Escherichia coli* <br> *Aerobacter aerogenes* <br> *Klebsiella pneumoniae* | } The coliform bacteria |
| *Salmonella typhosa* <br> *Salmonella choleraesuis* <br> *Salmonella typhimurium* | } The Salmonellae |
| *Shigella dysenteriae* <br> *Shigella schmitzii* <br> *Shigella arabinotarda* <br> *Shigella flexneri* <br> *Shigella boydii* <br> *Shigella sonnei* | } The Shigellae |

| Other enteric bacilli | |
|---|---|
| *Proteus vulgaris* <br> *Proteus mirabilis* <br> *Proteus morgani* | } Proteus species |
| *Pseudomonas aeruginosa* <br> *Alcaligenes faecalis* <br> *Vibrio cholerae* | |

| Hemophilus-Bordetella group | |
|---|---|
| *Hemophilus influenzae,* | *H. ducreyi* <br> *H. hemophilus* <br> *H. aegypticus* <br> *H. paraiufluenzae* |
| *Bordetella pertussis* | |

Pasteurellae

*Pasteurella pestis*
*Pasteurella tulareusis*

Brucellae

*Brucella melitensis*
*Brucella abortus*
*Brucella suis*

Aerobic Spore-forming Bacilli

*Bacillus anthracis*
*Bacillus subtilis*
*Bacillus megaterium*
*Bacillus cereus*

Anaerobic Spore-forming Bacilli

*Clostridium botulinum*
*Clostridium tetani*
*Clostridium perfringens*
*Clostridium novyi*
*Clostridium septicum*
*Clostridium histolyticum*
*Clostridium tertium*
*Clostridium bifermentans*
*Clostridium sporogenes*

Mycobacteria

*Mycobacterium tuberculosis hominis*
*Mycobacterium bovis*
*Mycobacterium avium*
*Mycobacterium leprae*
*Mycobacterium paratuberculosis*

Actinomycetes (fungus-like bacteria)

*Actinomyces israelii*
*Actinomyces bovis*
*Actinomyces naeslundii*
*Nocardia asteroides*
*Nocardia brasiliensis*

| The Spirochetes | |
|---|---|
| *Treponema pallidum* | *Spirillum minus* |
| *Treponema pertenue* | *Streptobacillus moniliformis* |
| *Treponema carateum* | |
| *Borrelia recurrentis* | |
| *Leptospira icterohemorrhagiae* | |
| *Leptospira canicola* | |

Mycoplasmas

*Mycoplasma pneumoniae*

Other pathogens

*Listeria monocytogenes*
*Erysipelothrix rhusiopathiae*
*Streptobacillus moniliformis*
*Donvania granulomatis*
*Bartonella bacilliformis*

Rickettsiae (bacteria-like parasites)

*Rickettsia prowazekii*
*Rickettsia mooseri*
*Rickettsia rickettsii*
*Rickettsia conori*
*Rickettsia australis*
*Rickettsia sibiricus*
*Rickettsia akari*
*Rickettsia tsutsugamushi*
*Rickettsia burnetii*

*Rickettsia quintana*
Chlamydia (unclassifiable parasites bacterial/viral)
  Chlamydia agents (naming uncertain)

Fungi

*Cryptococcus neoformans*
*Blastomyces dermatidis*
*Histoplasma capsulatum*
*Coccidioides immitis*
*Paracoccidioides brasiliensis*
*Candida albicans*
*Aspergillus fumigatus*
Mucor corymbifer (Absidia corymbifera)
*Rhizopus oryzae*  ⎫
*Rhizopus arrhizus*  ⎬ Phycomycetes
*Rhizopus nigricans*  ⎭
*Sporotrichum schenkii*
*Fonsecaea pedrosoi*
*Fonsecaea compacta*
*Fonsecaea dermatitidis*
*Cladosporium carrionii*
*Phialophora verrucosa*
*Aspergillus nidulans*
*Madurella mycetomi*
*Madurella grisea*
*Allescheria boydii*
*Phialosphora jeanselmei*
*Microsporum gypseum*
*Trichophyton mentagrophytes*
*Keratinomyces ajelloi*
*Microsporum canis*
*Trichophyton rubrum*
*Microsporum andouini*

Viruses

Adenoviruses

Herpes viruses

Herpes simplex
Varicella (Chicken pox)
Herpes Zoster (Shingles)
Virus B
Cytomegalovirus

Pox Viruses

Variola (smallpox)
Vaccinia
*Poxvirus bovis*
Paravaccinia
*Molluscum contagiosum*

Picornaviruses

Poliovirus
Coxsackievirus
Echoviruses
Rhinoviruses

Myxoviruses

Influenza (A, B, and C)
Parainfluenza (1-4)
Mumps Virus
Newcastle Disease Virus
Measles Virus
Rinderpest Virus
Canine Distemper Virus
Respiratory Syncytial Virus
Rubella Virus

Arboviruses

Eastern Equine Eucephalitis Virus
Western Equine Eucephalitis Virus
Sindbis Virus
Chikungunya Virus
Semliki Forest Virus
Mayora Virus
St. Louis Encephalitis Virus
California Encephalitis Virus
Colorado Tick Fever Virus
Yellow Fever Virus
Dengue Virus

Reoviruses

Reovirus Types 1-3

Hepatitis

Hepatitis A Virus
Hepatitis B Virus

Tumor Viruses

Rauscher Leukemia Virus
Gross Virus
Maloney Leukemia Virus

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids; isoquinoline alkaloids; quinoline alkaloids; which includes quinine and quinidine; diterpene alkaloids, their derivatives and metabolites.

The next group of drugs includes steroids, which includes the estrogens, gestrogens, and androgens, andrenocortical, bile acids, cardiotonic glycosides and aglycones, which includes digoxigenin, saponins and sapogenins, their derivatives and metabolites. Also included are the steroid mimetic substances, such as diethyl stilbestrol.

The next group of drugs is cyclic lactams having from 5 to 6 membered rings, which include the barbiturates, diphenyl hydantoin, and their metabolites.

The next group of drugs is aminoalkyl benzenes, with alkyl of from 2 to 3 carbon atoms, which includes the amphetamines, catecholamines, which includes ephedrine, L-dopa, epinephrine, narceine, papaverine, their metabolites and derivatives.

The next group of drugs is benzheterocyclics which include oxazepam, chloropromazine, tegretol, imipramine, their derivatives and metabolites, the heterocyclic rings being azepines, dazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, C, D, E and K.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propanolol, griseofulvin, butyrophenones, antihistamines, anticholinergic drugs, such as atropine, their metabolites and derivatives.

The next group of compounds is amino acids and small peptides which include thyroxin, triiodothyronine, oxytocin, ACTH, angiotensin, gentamycin, met- and leu-enkephalin their metabolites and derivatives.

Metabolites related to diseased states include spermine, galactose, phenylpyruvic acid, and porphyrin type 1.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins IgA, IgG, IgE and IgM, the molecular weights will generally vary from about 160,000 to about $10^6$. Enzymes will normally range from about 10,000 to 600,000 in molecular weight. Natural receptors vary widely, generally being at least about 25,000 molecular weight and may be $10^6$ or higher molecular weight, including such materials as avidin, thyroxine bind globulin, thyroxine binding prealbumin, transcortin, etc.

ENZYME-BOUND-LIGAND

The enzyme-bound-ligand is prepared by conjugating an enzyme with the ligand, either by using a difunctional reagent or by forming covalent bonds between functionalities naturally present in the ligand or the enzyme or introduced by modification of the ligand or the enzyme.

Conjugation of proteins, including enzymes, to a wide variety of materials, such as proteins, polysaccharides, nucleic acids, and the like, has found extensive exemplification in the literature. A wide variety of linking groups and linking functionalities may be employed. Conveniently, nonoxocarbonyl, oxocarbonyl, diazo, sulfonyl, oximino, imido, and thiono functionalities may be employed. With oxocarbonyl, reductive alkylation may be advantageously employed. The linking group between the functionalities may be a bond, but will more usually have at least one carbon atom, more usually at least two carbon atoms and not more than about 20 carbon atoms, more usually not more than about 12 carbon atoms. Methods for conjugating enzymes to proteins may be found in U.S. Pat. Nos. 3,791,932 and 3,839,153.

Methods for conjugating monoepitopic ligands may be found in U.S. Pat. No. 3,817,837, particularly columns 31 to 34 and in the working examples, which disclosure is incorporated herein by reference.

In preparing the enzyme-bound-ligands of the subject invention, it is desirable that a substantial proportion of the activity of the enzyme-bound-ligand be retained when the ligand of the enzyme-bound-ligand is substantially saturated with antiligand. Usually, at least about 20% of the original activity of the enzyme-bound-ligand is retained, preferably at least about 30%, and more preferably at least 50%. It is therefore desirable that enzymes be employed and enzyme-bound-ligands be prepared in manners which diminish deactivation of the enzyme by the binding of antiligand to ligand. While any enzyme may be employed, for the most part certain enzymes will be preferred. In choosing an enzyme, it will be desirable that the enzyme have a high turnover rate after conjugation, that the enzyme be capable of storage without significant loss of activity, that there be a covenient assay for the enzyme which allows for a spectrophotometric determination, and the pH for the optimum turnover rate be reasonably close to the pH optimum for binding of the antiligand to ligand. Of course, for the purpose of this invention, there must also be available a macromolecular enzyme inhibitor which is deterred from approaching the enzyme upon binding of antiligand to ligand. Also, it is desirable that the enzyme have substrates available which are not inhibited from approaching the enzyme active site as compared to the approach of the enzyme inhibitor to the enzyme. Usually, the substrates will have molecular weights below 5,000, more usually below about 2,000, and preferably below about 1,000.

Of the various enzymes, the following table indicates enzymes of particular interest set forth in accordance with the I.U.B. classification.

1. Oxidoreductases
   1.1 Acting on the CH-OH group of donors
      1.1.1 With NAD or NADP as acceptor
         1. alcohol dehydrogenase
         6. glycerol dehydrogenase
         26. glyoxylate reductase
         27. L-lactate dehydrogenase
         37. malate dehydrogenase
         49. glucose 6-phosphate dehydrogenase
         17. mannitol 1-phosphate dehydrogenase
      1.1.2 With cytochrome as an acceptor
         3. L-lactate dehydrogenase
      1.1.3 With O$_2$ as acceptor
         4. glucose oxidase
         9. galactose oxidase
   1.2 Acting on the CH-NH$_2$ group of donors
      1.4.3 With O$_2$ as acceptor
         2. L-amino acid oxidase
         3. D-amino acid oxidase
   1.6 Acting on reduced NAD or NADP as donor
      1.6.99 With other acceptors diaphorase
   1.10 Acting on diphenols and related substances as donors
      1.10.3 With O$_2$ as acceptor
         1. polyphenol oxidase
         3. ascorbate oxidase
   1.11 Acting on H$_2$O$_2$ as acceptor
      1.11.1
         6. catalase
         7. peroxidase
3. Hydrolases
   3.1 Acting on ester bonds
      3.1.1 Carboxylic ester hydrolases
         7. cholinesterase
      3.1.3 Phosphoric monoester hydrolases 1. alkaline phosphatase
3.1.4 Phosphoric diester hydrolases
  3. phospholipase C
3.2 Acting on glycosyl compounds
  3.2.1 Glycoside hydrolases
    α-amylase
    4. cellulase
    17. lysozyme
    23. β-galacotsidase
    27. amyloglucosidase
    31. β-glucuronidase
3.4 Acting on peptide bonds
  3.4.2 Peptidyl-amino acid hydrolase
    1. carboxypeptidase A
  3.4.4 Peptidyl-peptide hydrolase
    5. α-chymotrypsin
    10. papain
3.5 Acting on C-N bonds other than peptide bonds
  3.5.1 In linear amides
    5. urease
3.6 Acting on acid anhydride bonds
  3.6.1 In phosphoryl-containing anhydrides
    1. inorganic pyrophosphatase
4. Lyases
  4.1 Carbon-carbon lyases
    4.1.2 Aldehyde lyases
  4.2 Carbon-oxygen lyases
    4.2.1 Hydrolases
      1. carbonic anhydrase
  4.3 Carbon-nitrogen lyases
    4.3.1 Ammonia lyases
      1. histidase

ENZYME INHIBITOR

The enzyme inhibitor is a macromolecular molecule which is capable of interacting with or reacting with the enzyme so as to substantially diminish the turnover rate of the enzyme, preferably to 0. The enzyme inhibitor can achieve its effect either physically or chemically.

Physical inhibition can occur in two different ways. In one way, the physical bulk of the inhibitor prevents the approach of the enzyme substrate. In another way, the binding of the enzyme inhibitor to the enzyme results in a conformational change, which affects the enzyme activity. In some instances, both of these effects may be present. For the most part, the physical inhibitors will be antibodies which bond to the enzyme (antienzyme). Either the whole antibody or Fab fragments may be employed. A number of antibodies which inhibit enzymes are commercially available and individual enzymes can be employed as antigens for the production of inhibitory antienzymes.

The other method for inhibiting the enzyme is by chemical reaction between the inhibitor and the enzyme. Particularly, inhibitors can be employed which react with the enzyme to diminish or destroy the enzymatic activity. A wide variety of irreversible inhibitors (inactivators) specific for particular enzymes are known and may be employed to the extent that they can be derivatized to macromolecular hub molecules and retain their inhibitory activity.

The following table indicates a number of known inhibitors and the enzymes which they inhibit.

| Enzyme | Inhibitor |
| --- | --- |
| γ-cystathionase | 2-amino-4-pentinoic acid (I) |
| | 2-amino-4-chloro-4-pentenoic acid (II) |
| alanine racemase | 3-3-dichloroalanine (III) |
| | 3,3,3-trichloroalanine (IV) |
| | (IV) |
| | D-cycloserine |
| tryptophanase | (IV) |
| tryptophan synthase (β₂) & (α₂β₂) | (IV) |
| lactate oxidase | 2-hydroxyl-3-butinoic acid |
| monoamine oxidase | N,N-trimethyl 2-propinylamine |
| | β-aminopropionitrile |
| plasma amine oxidase | 2-bromoethylamine |
| | 2-propinylamine |
| | 2-chlorallylamine |
| | phenyl glycine |
| | p-nitrophenyl glycine |
| | aminoacetonitrile |
| β-cystathionase | (IV) |
| | 2-amino-3-hydroxypropyl-1 |
| | 3'-carboxy-3'-amino-1'-propenyl-1-ethe |
| aspartate aminotransferase | L-2-amino-4-methoxy-trans-3-butenoic acid |
| γ-aminobutyric acid-α-ketoglutarate transaminase | ethanolamine O-sulfate |
| formylglycinamid ribonucleotide amidotransferase | albiziin |
| | azaserine |
| | diazooxonorleucine |
| | diazooxonanorvaline |
| traspeptidase (membrane bound) | 6-aminopenicillanic acid |
| | Δ³-7-aminocephalosporinic acid |
| B₆-linked enzymes | mimosine |
| serine protease | physostigime |
| glutamine synthetase | methionine sulfoximine |
| | wildfire toxin |
| nucleotide requiring enzymes e.g. malate dehydrogenase and lactate dehydrogenase | Blue Dextran (Wilson, Biochem. and Biophys. Res. Comm. 72, 816 (1976)) |
| peroxidase | o-dianisidine-dextran |

While competitive reversible inhibitors can be employed, there are not preferred, since they will be competing with substrate for enzyme with varying degrees of effectiveness in reducing the enzymatic rate of enzymes present in unbound enzyme labeled receptor.

Besides the specific enzymes listed above there will be many related enzymes which can be inactivated by the same irreversible inhibitors. Also, many derivatives of the noncompetitive inhibitors can be prepared which will be capable of inhibition, by retention of the active portion of the molecule.

Where the inhibitor is not a macromolecule, that is a molecule having at least a molecular weight greater than 2,000, normally greater than 5,000, the inhibitor will be conjugated to a hub nucleus to provide the necessary size to inhibit its approach to the complex. In conjugating the inhibitor to a hub nucleus, a site for linking will be chosen distant from the portion of the inhibitor which is involved in the inhibition. It will therefore normally be preferable to employ inhibitors which have sites which are not critical to the inhibitor and act with enzymes which are not too specific in their structural requirements for substrates. The following are illustrative of inhibitors conjugated to protein molecules and the enzymes which are inhibited.

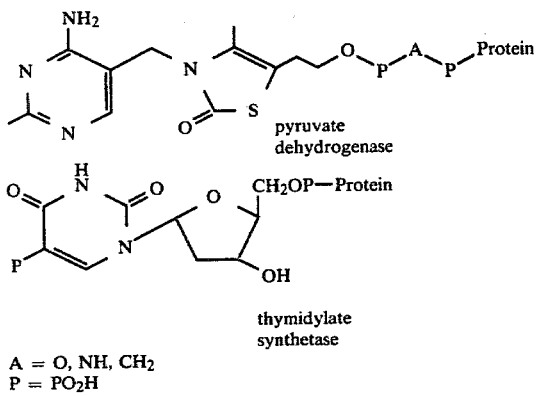

A = O, NH, CH$_2$
P = PO$_2$H

Conventional modes of linking may be employed for linking the inhibitor to a macromolecular species. The mode of linking will depend upon the particular inhibitor and the nature of the hub nucleus. In some instances, it may be feasible to have noncovalent binding of the inhibitor to a macromolecular species, where there is strong specific or nonspecific binding to the hub nucleus, which still allows for the inhibition.

The following examples are offered by way of illustration and not by way of limitation.

EXPERIMENTAL (All temperatures not otherwise indicated are in centigrade. All percents and parts not otherwise indicated are by weight, except for mixtures of liquids which are by volume. Unless otherwise indicated, materials employed in the various reactions are commercially available. The following abbreviations have the meaning indicated: DMF-dimethylformamide; THF-tetrahydrofuran; G-6-PDH-glucose-6-phosphate dehydrogenase; BSA-bovine serum albumin; RSA-rabbit serum albumin; HRP-horseradish peroxidase; T-3-triiodothyronine)

EXAMPLE 1.

Conjugation of triiodothyronine amidified with N-methyl-N, N-dicarboxymethyl amine anhydride with G6PDH(L. mesenteroides).

A. The reaction was carried out in a 25 ml round bottom flask wrapped in foil, equipped for magnetic stirring and placed under an argon atmosphere. A solution of 0.591 g T$_3$-methyl ester hydrochloride was formed in a solvent system consisting of 2 ml DMF and 2 ml THF. To this solution was added 146 μl of triethylamine (1.25 eq) and the solution stirred for fifteen minutes. Then 0.130 g (1.20 eq) of N-methyliminodiacetic acid anhydride (MEMIDA anhydride) was added in a single portion. When TLC on SiO$_2$ showed complete reaction, (the solvent system for TLC analysis was AcOH/MeOH/CHCl$_3$: 5:10:85.), the solvent was removed on a Büchi rotoevaporator initially using a water aspirator and finally a mechanical vacuum pump. The water bath temperature was not allowed to exceed 30°. The residue was dissolved in 8.5 ml dry THF. To the solution was added 76 ml of ethyl acetate and the mixture vigorously shaken. The resulting suspension was gravity filtered and the filtrate washed in a separatory funnel with 10 ml water, then 20 ml water, then 2×15 ml of a saturated salt solution to dry the solution. Further drying was effected with MgSO$_4$ which was then removed by gravity filtration. The solvent was removed on the evaporator and the product residue suspended in CHCl$_3$. Petroleum ether was then added as cosolvent in the suspension. The solvent was then removed by filtration and the solid product was dried in a desiccator under vacuum. After drying in the desiccator, 0.346 g of a white powder of T-3 MEMIDA was obtained.

B. Into 1 ml of THF was dissolved $2.21 \times 10^{-2}$ g of N-hydroxy succinimide and into a separate 1 ml of dry THF was dissolved $3.61 \times 10^{-2}$ g of dicyclohexylcarbodiimide. Into a reaction flask was charged 7 mg of the T$_3$-MEMIDA prepared above, 344 μl of dry THF, the reaction mixture cooled to ice bath temperature, followed by the addition of 46 μl of the NHS solution and 55 μl of the DCC solution. The reaction mixture was protected from light and was agitated in the cold room (2°) for about 27 hrs. The solution was stripped to driness in vacuo after filtering through a glass wool plug and the resulting white solid dissolved in approximately 1 ml of 20% n-hexane in CH$_2$Cl$_2$ and chromatographed on a 0.6×4.5 cm cellulose powder column in the same solvent and eluted with the same solvent using gravity flow. Approximately 2 column volumes of the developing solvent was employed and about 0.25 ml fractions were collected. Fraction 2-5 were combined, reduced to dryness and the residue dissolved in dry diglyme.

C. Into 2 ml of cold 0.05 M carbonate buffer, pH 9, was dissolved 12.1 mg of lyophilized G-6-PDH (L. mesenteriodes) and the solution dialyzed 1×350 ml with the same buffer overnight. The residue in the dialysis bag was adjusted to 3 ml with dialysate.

The solution was adjusted with the same buffer to a concentration of 2.16 mg/ml of the enzyme and 3 ml of the solution introduced into a reaction flask equipped with stirrer and the solution cooled in an ice bath. While cooling the mixture, 1 ml of DMF was added at a rate of 150 μl per minute, and then 1 ml was withdrawn. To the remaining 3 ml was added according to the following schedule T$_3$-MEMIDA NHS ester at a concentration of 0.385 equivalents per microliter. Two additions were made of 10 μl, followed by 1 addition of 20 μl, followed by 2 additions of 30 μl with 20 min. intervals between additions. After each addition, the enzyme activity in the presence and absence of anti (T-3) was assayed. The reaction mixture was placed in a 23 mm (25,000 mw cut-off) Spectrapor dialysis bag and dialyzed against 2×0.5 l. of 0.05 M tris-HCl, 0.1 M KCl, and 1 mM NaN$_3$, pH 8.0, in the cold room. The dialysis was repeated. After spinning down the dialysis residue at 15,000 rpm at 2° for 10 min., the supernatant was chromatographed on a 0.9×98.5 cm G-50 M column in 0.05 M tris-HCl, 0.1 M KCl, 1 mM NaN$_3$, pH 8.0, and eluted with the same buffer at a flow rate of 4 drops/min., collecting 20 drop fractions. Fractions 29-33 were combined and spun down at 17,000 rpm for 10 min. at 1°.

Into a cold Pierce Reactivial equipped with a stirring bar was introduced 3 ml of the above solution and 1 ml of cold 4 M neutralized hydroxylamine in water added slowly over a 5 min. period with stirring. After 10 min. at ice bath temperature, the reaction was allowed to continue for an additional 90 min. at room temperature. The reaction mixture was chromatographed on a Sephadex G-50 M column in the tris-buffer previously described and eluted with the same buffer at room temperature, employing a 0.9×98 cm column with a flow rate of 4 drops/min., collecting 20 drop fractions. Fractions 29 to 34 were combined and concentrated in the cold room using a collodion bag apparatus with a 25,000 molecular weight cut-off. The residue was adjusted to 2 ml with tris-HCl buffer as described previously. A 1 ml aliquot was dialyzed 2×250 ml with cold 50 mM carbonate buffer, pH 9.05.

Based on a Lowry protein determination and a radioactive count (the MEMIDA had $^{14}C$), the number of $T_3$ groups per enzyme was calculated to be about 16.

EXAMPLE 2.

Preparation of the conjugate of digoxin and G-6-PDH

A. A clear solution of 3-ketodigoxigenin (228 mg, 0.59 mmoles), carboxymethoxylamine hydrochoride (140 mg, 0.64 mmole) and sodium acetate (294 mg, 3.6 mmole) in methanol (18 ml, dried over molecular sieves 3A) was stirred at room temperature under nitrogen for 3 hours. The tlc of an aliquot showed the complete formation of oxime derivative ($R_f$0.33; 0.5:1:10/HOAc-MeOH-CHCl$_3$, Silica gel plate). The resulting reaction product was stripped to dryness, the residue dissolved in 32 ml 5% NaHCO$_3$ at 5°–10°, and extracted with 3×20 ml chloroform. The bicarbonate layer was acidified at 5°–10° with 28 ml of 1 N hydrochloric acid to pH 2–3 and extracted with 10×25 ml ethyl acetate. The ethyl acetate extracts were washed with saturated sodium chloride and dried over anhydrous sodium sulfate. Evaporation of solvent gave a solid which was recrystallized from a mixture of methanol-ethyl acetate-hexane to yield a white solid (188 mg, mp. 202°–220° (dec)).

B. To a dry flask, fitted with serum stopper and drying tube was introduced 23.05 mg (0.05 mmole) of the oxime and 250 μl of DMF (dried over 4 A° molecular sieves) and 7.1 μl (0.052 mmole) of dry triethylamine added through the serum stopper with a syringe with stirring at room temperature. After cooling the mixture to −14°, 9.34 μl (0.05 mmole) of carbitol chloroformate was added below the surface of the solution and the mixture stirred for 30 minutes.

In a separate flask, to 2 ml of glucose-6-phosphate dehydrogenase (G6PDH) at a concentration of about 1-2 mg/ml in 0.055 M tris buffer, pH 8.1, with stirring is added 20 mg of glucose-6-phosphate disodium salt and 40 mg NADH. (During the reaction aliquots are taken and the enzyme activity is determined by diluting a 5 μl aliquot of the enzyme solution to 5 ml, and taking a 50 μl aliquot of the diluted enzyme solution and diluting with 1 ml buffer and 50 μl substrate, introducing the solution into a 1.5 ml sample cup and employing a flow cell, reading the enzyme activity over a 60 second interval in a Gilford spectrophotometer.) The mixture is cooled to 0° and with stirring 1.08 ml carbitol added slowly with a syringe below the surface of the solution. After standing for 30 minutes, any precipitate is removed by centrifuging for 4 minutes with a Brinkman centrifuge and isolating the supernatant. The supernatant is adjusted to a pH of about 9.0 with 1 N NaOH. The enzyme activity is checked at this time.

To a stirring solution of the enzyme, 1 μl aliquots of the mixed anhydride prepared above are added to the enzyme at a rate of about 1 μl per minute. After the addition of 10 μl of the mixed anyhdride, the percent inhibition and the percent deactivation are determined. Percent inhibition is determined by employing approximately 5 μl of full strength antidigoxin in the above assay. About 35–45 μl of the mixed anhydride are added to obtain an inhibition of about 50% and a deactivation of about 36%. When the desired inhibition and deactivation are obtained, the enzyme conjugate is purified by dialysis against 0.055 M tris-HCl buffer, pH 8.1 containing 0.05% NaN$_3$ and 0.005% Thimerosal.

Following the above described procedure, in a first reaction, an enzyme conjugate was obtained having 5 digoxins conjugated to the enzyme, which was 36% deactivated and was 50% inhibited, while in a second reaction sequence, an enzyme conjugate was obtained having 9.2 digoxins, which was 48% deactivated and 62% inhibited.

EXAMPLE 3.

Conjugation of human gamma globulin (hIgG) to HRP.

A. Lyophilized HRP (10.95 g) was dissolved in 0.5 ml of 0.3 M NaHCO$_3$ buffer (pH 8.6) the solution placed in a dialysis bag and dialyzed against 1×500 ml of ice cold buffer (see above) in the cold room for 3 hrs. The pH was adjusted to 8.1 and the solution then dialyzed again for 4 hrs. The HRP solution volume was adjusted to 2 ml with dialysate and analyzed spectrophotometrically showing a concentration of 3.46 mg/ml.

B. To 1.5 ml of the above solution was added with stirring at room temperature 100 μl of a 1% solution in 95% ethanol of fluorodinitrobenzene and the mixture allowed to stir for one hour while shielded from direct light. Sodium periodate (1 ml, 40 mM), was added and the mixture stirred for 0.5 hr. under the same conditions, followed by the addition of 0.5 ml of 0.34 M aqueous ethylene glycol. After stirring for an additional hour under the same conditions, the reaction mixture was transferred to a dialysis bag and dialyzed against 3×900 ml of 10 mM NaHCO$_3$ buffer (pH 9.5) in the cold room.

C. Lyophilized hIgG (9.7 mg, Miles Laboratories, lyophilized and treated with DEAE-cellulose, lot No. 24) was dissolved in 0.5 ml of 10 mM NaHCO$_3$ buffer (pH 9.5) and dialyzed 2×500 ml of ice cold buffer (see above), The solution was adjusted to 1.2 ml with dialysate, then spun down with a Brinkman microcentrifuge for 4 min. at 2°–4° and analyzed spectrophotometrically showing a concentration of 5.28 mg/ml.

D. To the dialyzed residue of the HRP dialdehyde (5.2 mgHRP, $1.3 \times 10^{-1}$ μmole) was added with stirring at 2°–4°, 0.95 ml of the hIgG dialyzed residue (5 mg, $3.1 \times 10^{-2}$ μmole) and the mixture stirred for 45 min. To the mixture was then added 5 mg ($1.32 \times 10^{-4}$ mole) of NaBH$_4$, the mixture stirred for about 4.5 hrs. at 2°–4° and then dialyzed against 2×300 ml of PBS (10 mM Na$_2$HPO$_4$, 0.15 M NaCl, pH 7.0) in the cold room. The residue of the dialysis was further concentrated with a collodion bag apparatus (25,000 molecular weight cut-off) in the cold room to approximately 1 ml, spun down for 2 min. in a Brinkman microcentrifuge in the cold room and the supernatant chromatographed on a 1.5×89 cm Sephadex G-200 column (gel in PBS) and eluted with the same PBS buffer. The flow rate was 1 drop per 30 sec. and 20 drop fractions were collected. The operating pressure was 15 cm and the chromatography was carried out at room temperature.

The various fractions were analyzed both spectrophotometrically and for enzyme activity and fraction 48 showed $1.65 \times 10^{-6}$ M HRP and $1.32 \times 10^{-6}$ M hIgG for a ratio of hIgG to HRP of 0.80. The enzyme assay will be described subsequently.

EXAMPLE 4.

Conjugation of hIgG and G6PDH.

A. Into an ice cooled reaction flask was introduced 0.42 μmoles of [$^{14}$C]-hIgG in 0.5 M NaHCO$_3$ buffer, pH10 followed by the addition of 0.52 g ($4.2 \times 10^{-3}$ M) of ethyl acetimidate in 3 ml of deionized water adjusted to pH 10 with sodium hydroxide. After stirring for 5 min. at about 4°, the mixture was then stirred at room temperature for 25 min. A second addition of an equal amount of ethyl acetimidate was made following the same conditions as described for the first addition and the reaction solution transferred to a dialysis bag and dialyzed against $3 \times 1400$ ml at 2° against 0.5 M K$_2$HPO$_4$. After adjusting the pH to 7.8 with conc. hydrochloric acid, the solution in the bag was divided into 2 parts and centrifuged for 30 min. at 12 K at 2° in a Sorval centrifuge. The solution was then concentrated in a collodion bag apparatus versus PBS, pH 7.8.

A Sephadex G-200 column was prepared by first swelling the Sephadex G-200 in PBS, pH 6.7, by heating the mixture in a boiling water bath for 9 hrs. A $2 \times 89$ cm column was prepared and a portion of the above solution applied to the column. The fractions were eluted with PBS, pH 7.0 containing 0.02% NaN$_3$. The fraction collector was erratic, but fractions 113–145 were combined and dialyzed against 100 mM sodium phosphate, pH 8.0, $1 \times 1200$ ml, $2 \times 1000$ ml, the initial volume being 38 ml and the final volume being 35 ml. The solution was then concentrated to 6.2 ml on a collodion bag apparatus to give a solution 2.36 mg/ml hIgG.

B. To 1 ml of the above solution ($1.48 \times 10^{-8}$ mole hIgG) was added 1 ml of 0.06 M sodium periodate ($6 \times 10^{-5}$ mole) in water at pH 8.1 and the mixture stirred for 3.5 hrs. at room temperature. To the mixture was then added 1 ml of 0.16 M aqueous ethylene glycol and the mixture stirred for 1.5 hrs. at room temperature. The reaction mixture was then transferred to a dialysis bag and dialyzed against $3 \times 500$ ml of 50 mM NaHCO$_3$ buffer, pH 9, followed by dialysis against $1 \times 500$ ml of 200 mM NaHCO$_3$ buffer, pH 8.8.

C. Approximately 3.5 ml of G-6-PDH (L. mesenteroides, lot No. 6A053-402) was dialyzed exhaustively with 200 ml of 200 mM NaHCO$_3$ buffer, pH 8.8.

The hIgG (2.27 mg, $1.42 \times 10^{-8}$ mole) and G-6-PDH (8.82 mg, $8.48 \times 10^{-8}$ mole) solutions were combined to provide a final volume of 6.6 ml which was stirred while cooled in an ice bath. The mixture was then allowed to warm to room temperature and stirring continued for 4 hrs. After cooling the mixture in an ice water bath, 5 mg of NaBH$_4$ were added and the mixture maintained in an ice bath for 3.5 hrs. The solution was then transferred to the dialysis bag and exhaustively dialyzed at 2°–4° against a buffer solution, 10 mM K$_2$HPO$_4$ containing 0.15 M NaCl, pH 9. The reaction mixture was then concentrated in a collodion bag apparatus versus PBS, pH 7.0 to a volume of 2.4 ml.

A $2 \times 84$ cm chromatographic column was prepared of Sephadex G-200 in a PBS, pH 7.0. The reaction mixture was applied to the column and eluted with PBS, pH 7.0, at room temperature, coolecting 40 drop fractions. The column flow rate was 5 drops/min, employing a pressure head of about 18 cm. The fractions were assayed for enzyme activity as well as for radioactivity. The enzyme assay method will be described subsequently.

EXAMPLE 5.

Conjugation of o-dianisine to Dextran 10

To 0.5 g of Dextran 10 in 2 ml H$_2$O cooled to 4° was added 250 μl of 100 mg/ml CNBr in H$_2$O at 4° and the pH maintained at 11 by continuous addition of 1 N NaOH. After 5 min. a 200 μl aliquot was taken, 2 ml acetone added and the solution centrifuged at 10 K for 5 min at 4° and the pellet isolated. The pellet was dissolved in a mixture of DMF/0.1 M bicarbonate buffer, pH9 and a 20 mg/ml solution of o-dianisidine in the same mixture added to provide a 1:10 mole ratio of the Dextran 10 to the o-dianisidine. The pH was adjusted to 9 and the reaction allowed to proceed overnight in the dark with gentle stirring.

To the mixture was then added 100 μl of 1 M aqueous 1-amino-2-propanol, the pH adjusted to 9 with 1 N HCl and the mixture allowed to stand at room temperature in the dark for 3 hrs. The pH was then adjusted to 7, centrifuged at 10 K for 5 min. at 4° and the supernatant isolated.

To a Sephadex G-25 $2 \times 40$ cm column in 0.01 M PO$_4$, 0.2 M NaCl, pH7 buffer was added the above supernatant and the product eluted with the same buffer at a rate of 35 ml/hr collecting 80 drop fractions while maintaining the column in the dark. Fractions 21 to 25 were collected and pooled.

In order to demonstrate the utility of the subject invention, a number of assays were carried out. It should be appreciated, that in many instances, the materials employed were not optimum for optimizing the sensitivity of the assay. Rather, synthetic convenience, availability and the early stages of the development have governed the nature and the results of the assays.

The first assay to be described employs the T-3 conjugate to glucose-6-phosphate dihydrogenase. To 5 μl of a 1:10 dilution of the product of Example 1 in 50 mM tris-HCl plus 0.1% RSA (pH 7.9) is added the following: 1.8 ml of an aqueous solution 50 mM in tris-HCl, 0.1% RSA, pH 7.9, 50 μl of 0.1 M β-NAD, pH 5.0 and 25 μl of anti T3 serum. The solution was incubated for 20 min. at 30° and then 100 μl of 0.066 M G-6-P in assay buffer without RSA and 2 μl of anti G-6-PDH in 25 μl buffer added in that order and assayed at 340 nm at 30°. The rate was followed for 4 min. The assay was repeated except that 25 μl of buffer was substituted for the 25 μl of anti T3. At the end of 4 min., the absorbance at 340 nm in the absence of anti T3 was 0.012, while in the presence of anti T3 was 0.020. The above results show that one can determine the amount of antiligand, in this case anti T3, in accordance with the subject technique. It should further be appreciated thart the enzyme conjugate had only 5.7 percent of the original enzyme activity and had a hapten number of about 16. The presence of the large number of haptens per enzyme as well as the low activity has the effect of substantially diminishing the sensitivity of the assay.

The next assay which was carried out concerns an assay for digoxin employing the product of Example 2. In performing the assay, $5.57 \times 10^{-3}$ g ($7.13 \times 10^{-6}$ mole) of digoxin was dissolved in 10 ml dry DMF and a series of dilutions performed on aliquots from the DMF solution. The assay was performed by diluting 25 μl of the digoxin-G-6-PDH conjugate with 1 ml of buffer. (The buffer is prepared by dissolving 0.25 g egg albumin in 250 ml of an aqueous solution 50 mM in tris-HCl and 1 mM NaN$_3$ (pH 7.8) to give a 0.1% egg albumin solution at pH 7.8). To the solution was then added a preincubated mixture of 25 μl antidigoxin (1 μl of antidigoxin diluted with buffer) 1 ml of assay buffer and 2 μl of the digoxin solution. After incubating for 10 min. at 30°, 50 μl of 80 mM β-NAD (pH 5.1) at 30° is added, the mixture assayed for 0.5 min. at 340 nm, 30°, followed by adding 5 μl of anti G-6-PDH and assaying at 340 nm, 30° for 5.5 min. The following table indicates the results.

TABLE I

| Sample+ No. | Digoxin, M × 6.77 in assay) | v¹* | v²* |
|---|---|---|---|
| 1 | 0 | 36.5 ± 0.5 | 38.8 ± 0.7 |
| 2 | × 10⁻⁹ | 43.0 ± 0.5 | 33.0 ± 0.3 |
| 3 | × 10⁻⁸ | 56.0 ± 0.5 | 19.3 ± 0.7 |
| 4 | × 10⁻⁷ | 59.5 ± 0.5 | 15.0 ± 1.0 |

*$v^1$ is the difference in absorbance over the first 0.5min;
$v^2$ is the difference in absorbance over the next 5.5min. The results are reported as the average of two readings and are corrected for background.
+ Concentration in assay solution
Digoxin-G-6-PDH conjugate   $4.3 \times 10^{-10}$M
Anti(digoxin)   $\sim 0 \times 10^{-8}$M The results observed with $v^2$ demonstrate that the concentration of digoxin can be determined over a $10^4$ range at concentrations as low as about $10^{-8}$ to $10^{-9}$ M in digoxin.

The next assay demonstrates the use of the subject invention for determination of antigens as compared to the above haptens. The photocol for this assay is to dilute 2 μl of the HRP-hIgG conjugate with 200 μl of buffer to which is added 20 μl of hIgG and 2 μl of anti hIgG. The mixture is incubated for 0.5 hrs. at 30° followed by the addition of 4 μl of anti-HRP and incubation for an additional 0.5 hrs. To the mixture is then added 1.8 ml of buffer having 0.22 mM o-dianisidine in the buffer and 10 ml of 22 mM hydrogen peroxide and the change in absorance at 460 nm at 30° over one minute determined from commencement of reaction. The final concentrations are $1.3 \times 10^{-9}$ M for the HRP-hIgG conjugate, $3.7 \times 10^{-8}$ M for anti-hIgG and $4.6 \times 10^8$ M for anti-HRP. The buffer employed is 0.01 M sodium phosphate, 0.05 M sodium sulfate, 0.1% egg albumin and 4.0% polyethylene glycol 6,000, pH 7.0.

The following table reports the results at various concentrations of hIgG.

TABLE II

| Sample No. | hIgG,M (in assay) | Rate in OD/min |
|---|---|---|
| 1 | 0 | 144, 144 |
| 2 | 1×10⁻⁷ | 96, 84 |
| 3 | 1×10⁻⁸ | 93, 87 |
| 4 | 1×10⁻⁹ | 123, 126 |
| 5 | 1×10⁻¹⁰ | 135, 138 |
| 6 | 1×10⁻¹¹ | 138, 138 |

It is evident from the above results, that a sensitive assay for human gamma globulin is provided, where concentrations can be detected at as low as $10^{-10}$ M. Furthermore, after a few simple additions and incubations, extending over about 0.5 hr., the determination can be rapidly made. Simple spectrophometric equipment can be employed and the reading made in the visible region.

The next assay is also for hIgG using the conjugate of Example 4, employing the enzyme G-6-PDH. Fraction 42 of that preparation is employed. The assay is carried out by preparing a mixture of 0.2 ml of fraction 42 in 0.2 ml of a $3.68 \times 10^{-5}$ M solution of anti-hIgG in buffer, 10 mM sodium phosphate and 50 mM sodium sulfate, pH 7.48. The concentration of hIgG in fraction 42 is $2.54 \times 10^{-2}$ mg/ml, while the concentration of G-6-PDH is $1.58 \times 10^{-2}$ mg/ml. The mixture is incubated at 30° for over 30 min. A solution is prepared of 1.6 ml buffer, 0.05 ml G-6-P and 0.05 ml NAD and incubated in a cuvette at 30° for 3 min. The buffer is 50 mM tris-HCl containing 0.1% RSA and 1 mM NaN₃, pH 7.8. The G-6-P solution is 140 mM in buffer without the RSA and the NAD solution is 80 mM in deionized water, pH 5. To the cuvette is then added 0.05 ml of the combined conjugate and anti-hIgG, which has been preincubated, the solutions mixed by inversion and read at 340 nm for 2.5 min. The reading is interrupted, 1 ||1 of anti G-6-PDH added to provide an excess of the anti G-6-PDH in the assay medium, the solution mixed by inversion and read at 340 nm for 5 min.

The procedure is repeated except that the 0.2 ml of anti-hIgG is substituted with 0.2 ml of PBS, pH 7.

The rate as determined between the first and second minute in change in milliabsorbance/min. in the absence of anti-G-6-PDH was 51.8 and between the 5th and 4th minute of the 5 min. period was 22.2 in the presence of anti-G-6-PDH, when anti(hIgG) was present. In the absence of anti(hIgG), the results were 52.4 and 2.3 respectively.

It is evident from the above results, that one can determine the presence of anti-hIgG at extremely low concentrations. Furthermore, from the result, one could further determine hIgG, since the presence of hIgG in the assay medium would have the effect of reducing the amount of anti-hIgG available for binding to the hIgG-G-6-PDH conjugate.

The following final assay also uses hIgG as exemplary of antigens and shows the effect of added antibody and the combination of antibody and antigen. The assay also demonstrates the use of an enzyme inhibitor-substrate which deactivates the enzyme, so that a stable observed value is obtained within a short period of time after all of the reagents have been added.

The protocol is as follows. The Dextran 10-o-dianisidine (0.5 ml) prepared in Ex. 5 is diluted 1:1 with the same buffer as used with HRP previously, a sufficient amount of HRP-hIgG conjugate added to provide a final concentration of $1.4 \times 10^{-8}$ M and, as appropriate, 20 μl of aqueous anti-hIgG (Miles Labs, Lot 20, 9.6 mg/ml) and hIgG (final concentration $10^{-6}$) added, followed by a 20 min incubation at room temperature. To the mixture is then added 5 μl 22 mM H₂O₂ and the change in absorbance at 460 nm at 30° over one minute determined. A second reading is taken at 10 min. where no further significant change in absorbance is noted. The following indicates the results.

TABLE III

| Ab(hIgG) | hIgG | mOD | |
|---|---|---|---|
| | | 1min. | 10min. |
| − | − | 362, 302 | 390, 365 |
| + | − | 230, 217 | 295, 295 |
| + | + | 328, 334 | 365, 365 |

The addition of anti(hIgG) substantially reduces the amount of o-dianisidine which is converted over a predetermined period of time. Addition of anti(hIgG) and hIgG reduces the available anti(hIgG) for binding to the enzyme conjugate and allows for greater conversion before the available enzyme is substantially deactivated. Employing this technique eliminates the need to carefully time the absorbance readings, since after a few minutes, the reading remains fairly constant for relatively long periods of time.

It is evident from the above results, that a sensitive and accurate method for determining extremely low concentration of ligands, including both haptenic and antigenic ligands, is provided. Furthermore, the subject method has the desirable aspect that enzymes can be lightly labeled, so as to retain a substantial proportion of their original activity, both after conjugation and when antiligand is bound to the conjugate. In addition, any adventitious presence of native enzyme will be inhibited, thus avoiding the need to determine the activity of the enzyme in the sample. The protocol is simple for the subject assay and spectrophotometers can be employed, which are generally available. Furthermore, determination is in effect an enzyme determination with which most technicans are generally familiar.

Although the foregoing invention has been described in some detail by way of illustration and example for purposes of clarity of understanding, it will be obvious that certain changes and modifications may be practiced within the scope of the appended claims.

What is claimed is:

1. A method for determining the presence in a sample of an analyte which is a member of an immunological pair consisting of ligand and ligand receptor which comprises:
    combining in an aqueous medium:
    (A) said sample;
    (B) enzyme-bound-ligand which retains a substantial proportion of its activity when bound to receptor;
    (C) ligand receptor, when ligand is the analyte, wherein said receptor is capable of specifically binding to said ligand and said enzyme-bound-ligand; and
    (D) enzyme inhibitor, of at least about 2,000 molecular weight wherein said inhibitor is impeded from inhibiting said enzyme-bound-ligand, when receptor is bound to enzyme-bound-ligand; and
    determining the enzymatic activity in said medium as compared to the enzymatic activity in a medium having a known amount of analyte.

2. A method according to claim 1, wherein said aqueous medium is at a pH in the range of about 5 to 10 and at a temperature in the range from about 10° to 50° C.

3. A method according to claim 2, wherein in a first step, said sample, enzyme-bound-ligand and antiligand are combined; and in a second step, enzyme inhibitor is added.

4. A method according to claim 1, wherein in a first step, said sample and ligand receptor are combined; in a second step enzyme-bound-ligand is added; and in a third step enzyme inhibitor is added.

5. A method according to claim 1, wherein said enzyme inhibitor is a reversible inhibitor.

6. A method according to claim 5, wherein said reversible inhibitor is an antienzyme.

7. A method according to claim 1, wherein said enzyme inhibitor is an irreversible inhibitor.

8. A method according to claim 7, wherein said irreversible inhibitor is a substrate for the enzyme of said enzyme-bound-ligand.

9. A method according to claim 1, wherein said analyte is a ligand of from about 5,000 to 1,000,000 molecular weight.

10. A method according to claim 9, wherein said ligand is a poly(amino acid) of from about 5,000 to 600,000 molecular weight.

11. A method according to claim 1, wherein said analyte is a ligand of from about 125 to 5,000 molecular weight.

12. A method for determining the presence in a sample of a ligand which comprises:
    combining in an aqueous medium:
    (A) said sample;
    (B) enzyme-bound-ligand which retains a substantial proportion of its activity when bound to receptor;
    (C) ligand receptor, wherein said receptor is capable of specifically binding to said ligand and said enzyme-bound-ligand; and
    (D) antienzyme, wherein said antienzyme inhibits said enzyme-bound-ligand when bound to said enzyme and is impeded from binding to the enzyme of said enzyme-bound-ligand, when ligand receptor is bound to enzyme-bound-ligand; and
    determining the enzymatic activity in said medium as compared to the enzymatic activity in a medium having a known amount of ligand.

13. A method according to claim 12, wherein said aqueous medium is at a pH of from about 6 to 9 and at a temperature in the range of from about 10° to 50° C.

14. A method according to claim 13, wherein said ligand is an haptenic molecule of from about 125 to 2,000 molecular weight and said enzyme is glucose-6-phosphate dehydrogenase.

15. A method according to claim 14, wherein said ligand is digoxin.

16. A method according to claim 14, wherein said ligand is triiodothyronine.

17. A method for determining the presence in a sample of a ligand which comprises:
    combining in an aqueous medium:
    (A) said sample;
    (B) enzyme-bound-ligand, which retains a substantial proportion of its activity when bound to ligand receptor;
    (C) ligand receptor, wherein said receptor is capable of specifically binding to said ligand and said enzyme-bound-ligand; and
    (D) enzyme inhibitor, of at least about 5,000 molecular weight which is an enzyme substrate which reacts with said enzyme to inhibit said enzyme and is impeded from reacting with said enzyme when ligand receptor is bound to said enzyme-bound-ligand; and
    determining the enzymatic activity in said medium as compared to the enzymatic activity in a medium having a known amount of ligand.

18. A method according to claim 17, wherein said ligand is poly(amino acid) of from about 5,000 to 600,000 molecular weight and said enzyme is peroxidase.

19. A method according to claim 18, wherein said ligand is γ-globulin and said inhibitor is o-dianisidine bonded to a macromolecular hub nucleus.

20. An assay composition for use in the method according to claim 1 comprising enzyme-bound-ligand; ligand receptor and enzyme inhibitor of at least 2,000 molecular weight in relative proportions to at least substantially optimize the signal response to analyte, wherein the ratio based on binding sites of ligand receptor to enzyme-bound-ligand will be in the range of about 1–100:1, an equivalent ratio of enzyme-inhibitor to enzyme based on active sites will be in the range of about 0.1–100:1.

21. An assay composition according to claim 20, wherein said enzyme inhibitor is antienzyme.

22. An assay composition according to claim 20, wherein said enzyme inhibitor is a macromolecular inhibiting enzyme substrate.

23. An assay composition for use in the method according to claim 1 for determining antiligand comprising enzyme-bound-ligand and enzyme inhibitor of at least 2,000 molecular weight in relative proportions to at least substantially optimize the signal response to analyte, wherein the equivalent ratio of enzyme inhibitor to enzyme based on active sites will be in the range of about 0.1–100:1.

* * * * *